United States Patent
Van Geel et al.

(10) Patent No.: US 9,403,929 B2
(45) Date of Patent: Aug. 2, 2016

(54) PROCESS FOR PREPARING ACRYLIC POLYMER BEADS

(71) Applicant: DSM IP ASSETS B.V., Heerlen (NL)

(72) Inventors: Adrianus Antonius Johannes Van Geel, Basel (CH); Leopold Franciscus Wijnandus Vleugels, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/425,172

(22) PCT Filed: Aug. 12, 2013

(86) PCT No.: PCT/EP2013/066832
§ 371 (c)(1),
(2) Date: Mar. 2, 2015

(87) PCT Pub. No.: WO2014/044469
PCT Pub. Date: Mar. 27, 2014

(65) Prior Publication Data
US 2015/0232594 A1    Aug. 20, 2015

(30) Foreign Application Priority Data

Sep. 18, 2012   (EP) .................................... 12184839

(51) Int. Cl.
| C08F 220/14 | (2006.01) |
| C08F 220/18 | (2006.01) |
| A61K 8/04 | (2006.01) |
| A61Q 5/00 | (2006.01) |
| A61Q 5/06 | (2006.01) |
| A61K 8/81 | (2006.01) |
| C08F 220/06 | (2006.01) |

(52) U.S. Cl.
CPC ............... *C08F 220/14* (2013.01); *A61K 8/046* (2013.01); *A61K 8/8152* (2013.01); *A61Q 5/06* (2013.01); *C08F 220/06* (2013.01); *C08F 220/18* (2013.01)

(58) Field of Classification Search
CPC .... C08F 220/14; C08F 220/18; C08F 220/06; C08F 2220/1816; A61K 8/046; A61K 8/8152; A61Q 5/06
USPC .................................. 526/318.44; 424/70.16
See application file for complete search history.

(56) References Cited

U.S. PATENT DOCUMENTS 8,741,274 B2 *  6/2014  van Geel ................ A61K 8/046
                                                    424/70.16

FOREIGN PATENT DOCUMENTS

| CN | 102666614 | 9/2012 | | |
| EP | 2 322 570 | 5/2011 | | |
| GB | 1 312 098 | 4/1973 | | |
| JP | GB 1312098 A | * | 4/1973 | ............ C08F 220/12 |
| NL | EP 2322570 A1 | * | 5/2011 | ............ A61K 8/046 |

OTHER PUBLICATIONS

International Search Report for PCT/EP2013/066832 mailed Nov. 15, 2013, two pages.

* cited by examiner

*Primary Examiner* — Michael M Bernshteyn
(74) *Attorney, Agent, or Firm* — Nixon & Vanderhye P.C.

(57) ABSTRACT

The present invention relates to a novel process for the preparation of acrylic polymer beads, said process encompassing the step of washing the acrylic polymer beads with purified water.

14 Claims, No Drawings

PROCESS FOR PREPARING ACRYLIC POLYMER BEADS

This application is the U.S. National Phase of International Application No. PCT/EP2013/066832 filed 12 Aug. 2013 which designated the U.S. and claims priority to EP Patent Application No. 12184839.4 filed 18 Sep. 2012, the entire contents of each of which are hereby incorporated by reference.

The present invention relates to a novel process for the preparation of acrylic polymer beads, said process encompassing the step of washing the acrylic polymer beads with purified water.

Hair styling compositions are desired that provide both good hold and a natural feel and look. Additionally, clarity (translucent appearance) of the hair styling composition prior to application is aesthetically important to consumers.

Acrylic polymer beads exhibiting providing excellent hair styling benefits are e.g. known from EP2501730 A1. However, it has been discovered that these polymers after incorporation into ethanolic hair spray formulations render the formulations turbid which is highly unwanted by the cosmetic industry.

An object of the present invention was thus to identify means to overcome the above mentioned turbidity issue.

Surprisingly it has now been found that washing the isolated acrylic polymer beads with purified water overcomes the above mentioned problem.

Thus the invention relates in a first embodiment to a process for the preparation of acrylic polymers beads, said process comprising the steps (i) subjecting a monomer composition consisting of a mixture of methacrylic acid (MAA), n-butyl methacrylate (BMA), ethylacrylate (EA) and ethyl methacrylate (EMA) to suspension polymerization followed by (ii) isolating the resulting acrylic polymer beads followed by (iii) washing the acrylic polymer beads with purified water.

Purified water, by definition of the FDA, is water that is produced by distillation, deionization, reverse osmosis or other suitable processes and that meets the definition of "purified water" in the U.S. Pharmacopeia, 23d Revision, Jan. 1, 1995. As appropriate, also may be called "demineralized water," "deionized water," "distilled water," and "reverse osmosis water".

The term "purified water" as used herein refers to water obtainable by using e.g. standard ion-exchange or reversed osmosis equipment followed by the removal of colloidal particles by filtration. However a person skilled in the art may replace the process of ion exchange, without compromising its main action by distillation or reverse osmosis as long as the purified water contains less than 1 mg/kg of each of the following ions: $Na^+$, $K^+$, $NH_4^+$, $Ca^{2+}$ and $Mg^{2+}$. Preferably the concentration of each of the ions is less than 0.1 mg/kg. Most preferably, the purified water contains less than 0.1 mg/kg of $Na^+$, less than 0.5 mg/kg of $K^+$, less than 0.01 mg/kg $NH_4^+$, less than 0.01 mg/kg of $Ca^{2+}$ and less than 0.1 mg/kg of $Mg^{2+}$ ions.

In all embodiments of the present invention, the ratio (w/w) of purified water to the acrylic polymer beads used in the washing step is preferably selected in the range of 100:1 to 1:1, preferably in the range of 10:1 to 1:1 and most preferably in the range of 5:1 to 1.5:1.

After isolation of the beads in step (ii) according to standard methods such as filtration or centrifugation the beads may be subjected to a drying step, preferably at about 40-100° C. and more preferably at about 80-100° C. before the washing step. The drying can be performed by commonly known means to a person skilled in the art such as e.g. using a fluidized bed dryer or a conventional oven. The drying time can be easily adjusted by a person skilled in the art and is usually carried out over a period of 3 to 40 h such as about 8 to 20 h and in particular about 8 to 10 h. However, preferably the isolated beads are subjected to the washing step directly after isolation without an intermediate drying step.

After the washing step the acrylic polymer beads can be isolated and dried as outlined above. Thus, in another embodiment according to the present invention the process additional encompasses the step of isolating and drying the washed acrylic polymer beads of step (iii). Preferably the drying is carried out at about 40-100° C. and more preferably at about 60-80° C.

The preparation of acrylic polymer beads according to the present invention is e.g. disclosed in EP2501730 and in the examples herein. Furthermore, such polymeric acrylic beads are e.g. available at DSM Nutritional products Ltd. under the Tradename TILAMAR® Fix A1000 (INCI: Acrylates Copolymer, Chemical Name: polymer with 2-methyl-2-propenoic acid, butyl 2-methyl-2-propenoate, ethyl 2-methyl-2-propenoate and ethyl 2-propenoate, CAS Number: 1070166-98-1).

By the term "polymer beads" in connection with the present invention is meant polymer particles that are simple to isolate e.g. by filtering or centrifuging. The polymer beads in connection with the present invention typically have an average diameter of at least 50 μm, preferably at least 150 μm. Generally, the beads have a diameter between 50 and 1500 μm such as in particular between 150 to 400 μm.

In a particular embodiment the monomer composition consists of a mixture of 10-30 wt.-% of methacrylic acid, 35-65 wt.-% of n-butyl methacrylate, 5-15 wt.-% of ethyl acrylate and 10-35 wt-% of ethyl methacrylate such as in particular of 15-25 wt.-% of methacrylic acid, 38-60 wt.-% of n-butyl methacrylate, 8-15 wt.-% of ethyl acrylate and 15-25 wt.-% of ethyl methacrylate such as even more in particular of 17-22 wt.-% of methacrylic acid, 44-56 wt.-% of n-butyl methacrylate, 9-15 wt.-% of ethyl acrylate and 15-25 wt.-% of ethyl methacrylate. Most in particular low the monomer composition consists of 15-22 wt.-% of methacrylic acid, 44-56 wt.-% of n-butyl methacrylate, 9-15 wt.-% of ethyl acrylate and 18-22 wt.-% of ethyl methacrylate.

The term consisting of as used according to the present invention means that the total amount of monomers ideally sums up to 100 wt.-%. It is however not excluded that small amount of impurities or additives may be present such as e.g. in amounts of less than 5 wt.-%, preferably less than 3 wt.-% which are e.g. introduced via the respective raw materials.

Preferably the ratio of ethyl methacrylate (EMA) to ethyl acrylate (EA) (w/w) in the monomer compositions according to the invention and outlined above is selected in the range of 4:1 to 1:1, preferably in the range of 2:1 to 1:1, in particular in the range of 2:1 to 1.3:1.0, which can also be expressed as coefficient of EMA/EA which accordingly should preferably be selected in the range of 4 to 1, preferably in the range of 2 to 1 such as in particular in the range of about 2.0 to 1.3.

It is further preferred that the amount of methacrylic acid used in the monomer compositions according to the invention is less than 25 wt.-%, such as about 15 to 22 wt.-%, in particular about 17 to 22 wt.-% and even more in particular about 20 wt.-% based on the total amount of the monomers in order to further reduce the residual monomer content.

Particular preferred are monomer compositions wherein the MAA content is selected in the range of about 15-22 wt.-%, in particular 17 to 22 wt.-% and the coefficient of EMA/EA is selected in the range of about 2.0 to 1.3 as such polymer exhibit a good solubility in water or alcohols as well as mixtures thereof while having an extremely low residual monomer content.

The acrylic polymer beads made according to the present invention typically have a molecular weight of about 100 kDalton, a glass transition temperature of about 80-120° C. and a particle size of about 50 to 500 μm such as e.g. 200 to 500 μm (X-50). Due to high Tg of the acrylic polymer beads no anti-caking agent is needed to prevent the beads from sticking during storage even at elevated temperature. Furthermore, the residual monomer content prior to drying is low enough to come below the limit required for personal care applications after an extended drying step at about 80-100° C. such as e.g. at 90° C., i.e. below 250 ppm and in particular even below 100 ppm.

The acrylic polymer beads according to the invention typically have an acid value of about 125-145 mg KOH/g.

The glass transition temperature $T_g$ is the limit at which, according to G. Kanig (Kolloid-Zeitschrift & Zeitschrift fur Polymere, Vol. 190, page 1, equation 1) the polymer changes from a glassy, brittle state to a rubbery state. Tg values of polymers may e.g. be determined experimentally using techniques such as differential scanning calorimetry DSC.

The following examples are provided to further illustrate the processes and compositions of the present invention. These examples are illustrative only and are not intended to limit the scope of the invention in any way.

EXAMPLE 1

The polymerization reactions were conducted in a glass 3-necked reaction flask using stainless steel baffle and stirrer equipped with nitrogen inlet.

Hydroxylethylcellulose stabilizer (2.4 g) was weighed into the reaction flask containing distilled water (1,105 g). 480 g of a monomer mixture consisting of 240 g n-butylmethacrylate (BMA), 96 g ethylmethacrylate (EMA), 48 g ethylacrylate (EA) and 96 g methacrylic acid (MMA) was weighed into a separate stirred feedtank containing di-lauroylperoxide (3.6 g) as chain starter and dodecylmercaptane chain transfer agent (1.9 g). After homogenizing the feedtank, the mixture was transferred to the reaction flask and under constant nitrogen purge slowly heated to 75° C. This temperature was maintained for 4 hrs to reach hard bead stage. After establishing hard bead stage, reaction flask content was subsequently heated to 85° C. and left at this temperature for another 2 hrs. Accordingly the reactor contents were cooled, the final suspension polymer filtered, washed and allowed to dry at 40-50° C. for 14-16 hrs followed by an extended drying process at 90° C. for another 14-16 hrs yielding the acrylic polymer beads in 90-95% yield.

Afterwards the acrylic polymer beads obtained above were split in two portions and dispersed in purified water respectively TAP-water (Reference) in a ratio of polymer/water=1/2 (wt/wt) and left to mix for 1 hour at room temperature. Afterwards the water was separated from the polymer by centrifuging and the acrylic polymer beads were polymer placed in an oven at 70° C. for 16 hours to evaporate the excess moisture.

Purified water (DI-water) was obtained by using standard ion exchange. The ion content of the respective water grades is given in table 1

TABLE 1

| Ion | TAP-water [mg/kg] | DI-water [mg/kg] |
|---|---|---|
| $Na^+$ | 8.299 | 0.090 |
| $K^+$ | 2.443 | 0.021 |
| $NH_4^+$ | — | 0.003 |
| $Ca^{2+}$ | 23.181 | — |
| $Mg^{2+}$ | 2.576 | 0.048 |

After drying 5 wt.-% of each of the washed acrylic polymer beads were dissolved in pure ethanol and neutralized with AMP. The acrylic polymer beads washed with DI-water results in a clear solution, whereas the TAP-water washed acrylic polymer beads (Reference) resulted in a hazy solution.

The invention claimed is:

1. A process for the preparation of acrylic polymers beads, said process comprising the sequential steps of:
   (i) subjecting a monomer composition consisting of a mixture of methacrylic acid (MAA), n-butyl methacrylate (BMA), ethylacrylate (EA) and ethyl methacrylate (EMA) to suspension polymerization to form acrylic polymer beads, followed by
   (ii) isolating the acrylic polymer beads obtained in step (i), followed by
   (iii) washing the isolated acrylic polymer beads with purified water, wherein the purified water contains less than 1 mg/kg of each of the following ions: $Na^+$, $K^+$, $NH_4^+$, $Ca^{2+}$ and $Mg^{2+}$.

2. The process according to claim 1, wherein the purified water contains less than 0.1 mg/kg of $Na^+$, less than 0.5 mg/kg of $K^+$, less than 0.01 mg/kg $NH_4^+$, less than 0.01 mg/kg of $Ca^{2+}$ and less than 0.1 mg/kg of $Mg^{2+}$ ions.

3. The process according to claim 1, wherein step (iii) is practiced with a ratio (w/w) of the purified water to the acrylic polymer beads in a range of 100:1 to 1:1.

4. The process according to claim 1, wherein step (ii) is practiced by isolating the acrylic polymer beads by filtration or centrifugation.

5. The process according to claim 1, wherein the process further comprises the step of (iia) drying the isolated acrylic polymer beads obtained in step (ii) at 40-100° C.

6. The process according to claim 5, wherein the drying step (iia) is carried out over a period of 3 hours to 40 hours.

7. The process according to claim 1, wherein the process further comprises the step of (iiia) isolating the washed acrylic polymer beads of step (iii).

8. The process according to claim 1, wherein the monomer composition consists of a mixture of 10-30 wt. % of methacrylic acid, 35-65 wt.-% of n butyl methacrylate, 5-15 wt.-% of ethyl acrylate and 10 35 wt-% of ethyl methacrylate.

9. The process according to claim 1, wherein the monomer composition consists of a mixture of 17-22 wt.-% of methacrylic acid, 44-56 wt. % of n-butyl methacrylate, 9-15 wt.-% of ethyl acrylate and 15-25 wt.-% of ethyl methacrylate.

10. The process according to claim 1, wherein ethylmethacrylate (EMA) and ethylacrylate (EA) are present in the monomer composition in amount to achieve a coefficient of EMA to EA (w/w) in a range of 4 to 1.

11. The process according to claim 10, wherein the coefficient of EMA to EA (w/w) is in the range of 2 to 1.

12. The process according to claim 3, wherein the ratio (w/w) of the purified water to the acrylic polymer beads in a range of 10:1 to 1:1.

13. The process according to claim 5, wherein step (iia) is practiced by drying the isolated acrylic polymer beads at 80 to 100° C.

14. An ethanolic formulation which comprises the acrylic polymer beads prepared according to claim 1.

\* \* \* \* \*